US008775439B1

(12) United States Patent
Lasko et al.

(10) Patent No.: US 8,775,439 B1
(45) Date of Patent: Jul. 8, 2014

(54) IDENTIFYING ENTITIES USING SEARCH RESULTS

(75) Inventors: Thomas A. Lasko, Nashville, TN (US); Andrew Tomkins, San Jose, CA (US); Michael Angelo, San Francisco, CA (US); Matthew K. Gray, Reading, MA (US); Russell Ryan, Cambridge, MA (US); Namrata U. Godbole, Cambridge, MA (US); Roni F. Zeiger, Mountain View, CA (US)

(73) Assignee: Google Inc., Mountain View, CA (US)

( * ) Notice: Subject to any disclaimer, the term of this patent is extended or adjusted under 35 U.S.C. 154(b) by 100 days.

(21) Appl. No.: 13/246,745

(22) Filed: Sep. 27, 2011

(51) Int. Cl.
G06F 7/00 (2006.01)
G06F 17/30 (2006.01)

(52) U.S. Cl.
USPC .......................................... 707/748; 707/706

(58) Field of Classification Search
USPC ................................................ 707/706, 748
See application file for complete search history.

(56) References Cited

U.S. PATENT DOCUMENTS

| 6,006,242 | A | 12/1999 | Poole et al. |
|---|---|---|---|
| 6,510,425 | B1 | 1/2003 | Okamoto et al. |
| 7,043,492 | B1 | 5/2006 | Neal et al. |
| 7,519,529 | B1 | 4/2009 | Horvitz |
| 2005/0065813 | A1* | 3/2005 | Mishelevich et al. ............. 705/2 |
| 2007/0156032 | A1 | 7/2007 | Gordon et al. |
| 2008/0016048 | A1 | 1/2008 | Dettinger et al. |
| 2008/0184138 | A1 | 7/2008 | Krzanowski et al. |
| 2008/0208864 | A1 | 8/2008 | Cucerzan et al. |
| 2009/0259683 | A1* | 10/2009 | Murty .................... 707/999.003 |
| 2010/0312549 | A1 | 12/2010 | Akuwudike |
| 2011/0004609 | A1* | 1/2011 | Chitiveli et al. .............. 707/759 |
| 2011/0106895 | A1 | 5/2011 | Ventilla et al. |
| 2011/0270818 | A1 | 11/2011 | Chowdhury et al. |
| 2011/0314010 | A1 | 12/2011 | Ganti et al. |

OTHER PUBLICATIONS

Nadeau, et al., "A Survey of Named Entity Recognition and Classification", Lingvisticae Investigationes, vol. 30, No. 1, 2007, pp. 3-28(24).
Whitelaw, A., et al. Web-Scale Named Entity Recognition, Proceedings of the 17th ACM Conference on Information and Knowledge Management, Oct. 2008, pp. 123-132.
"Isabel System FAQs", Isabel Health Care [online] [retrieved on Oct. 23, 2012]. Retrieved from the Internet: <URL: http://www.isabelhealthcare.com/home/system_faq>, 2 pgs.

(Continued)

Primary Examiner — Charles Lu
(74) Attorney, Agent, or Firm — Fish & Richardson P.C.

(57) ABSTRACT

Methods, systems, and apparatus, including computer programs encoded on computer storage media, for identifying entities using search results. One of the methods includes the actions of determining that a first search query includes a respective text reference to each of one or more predetermined attributes, wherein each attribute is associated with a first entity type; for each of a plurality of entities of the first entity type, generating a combined search query that includes the first search query and a name of the entity; obtaining search results for each of the plurality of entities using the combined search query for each respective entity; and using the obtained search results to generate combined search results to include in a response to the first search query.

21 Claims, 9 Drawing Sheets

(56) References Cited

OTHER PUBLICATIONS

McGowen, J., et al., "Problem Knowledge Couplers: reengineering evidence-based medicine through interdisciplinary development, decision support, and research", Bull Med Libr Assoc, 87(4), Oct. 1999, [online] [retrieved on Oct. 23, 2012]. Retrieved from the Internet: <URL: http://www.ncbi.nlm.nih.gov/pmc/articles/PMC226622/pdf/mlab00089-0094.pdf, pp. 462-470.

* cited by examiner

IDENTIFYING ENTITIES USING SEARCH RESULTS

BACKGROUND

This specification relates to search systems.

The Internet provides access to a wide variety of resources, examples of which include video and audio files, web pages for particular subjects, book articles, and news articles. An Internet search engine can identify resources in response to a user query that includes one or more search terms or phrases. A search engine generally ranks the resources based on their relevance to the query and quality and provides search results that each include a link to an identified resource.

SUMMARY

This specification describes technologies relating to identifying entities that are answers to questions implied in search queries using search results.

Users may desire to use a search engine to identify entities that match features or attributes named in their queries. For example, a user listing symptoms in a query may wish to find medical conditions, e.g., diseases, disorders, injuries, and other health issues, that are characterized by the symptoms named in the query. The implicit question could be formulated as, what medical condition or medical conditions are associated with the named symptom or symptoms? Similarly, a user may wish to know what movie or movies feature an actor or actors, a director, or a producer named in a query. In other circumstances, a user may wish to find the movies or books that are about a topic or topics named in a query. More generally, the implicit question could be formulated as, what entity of a generic type, e.g., book, medical condition, or movie, is associated with the features named in the query?

In general, one innovative aspect of the subject matter described in this specification can be embodied in methods that include the actions of determining that a first search query includes a respective text reference to each of one or more predetermined attributes, wherein the attributes are each associated with a first entity type; for each of a plurality of entities of the first entity type, generating a combined search query that includes the first search query and a name of the entity; obtaining search results for each of the plurality of entities using the combined search queries; and using the obtained search results to select one or more entity names from among the names of the plurality of entities to include in a response to the search query.

Other embodiments of this aspect include corresponding systems, apparatus, and computer programs encoded on computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

These and other embodiments can each optionally include one or more of the following features. Determining that the first search query includes a respective text reference to each of one or more predetermined attributes can include: determining, only from text of the search query, that the first search query includes a respective text reference to each of one or more predetermined attributes. The one or more attributes can be medical symptoms and the first entity type can be medical conditions. The method can further include: receiving the first search query from a user device; and providing the selected names to the user device for presentation in a user interface, wherein the selected names are presented separately from search results for the first search query.

Using the obtained search results to select one or more entity names can include: for each of the plurality of entities, generating a summary score based on scores associated with search results obtained in response to the combined search query for the entity; and selecting the one or more entity names based on the summary scores. The method can further include: adjusting a summary score for a particular entity based on an inverse document frequency of the particular entity. Determining that the first search query includes a respective text reference to each of one or more attributes associated with the first entity type can include: determining that at least one term in the first search query appears in an attribute data store. The attribute data store can contain terms from previously submitted queries determined to relate to entities of the first entity type by a query classifier.

The method can further include: receiving a second search query from the user device, the second search query including a text reference to each of one or more additional attributes associated with entities of the first entity type; and refining the selected names based on the second search query. The method can further include: obtaining search results for the first search query; and determining that a number of the search results for the first search query that identify a resource related to the first entity type exceeds a specified threshold value. The method can further include: obtaining search results for the first search query; and determining that a measure of quality of the search results for the first search query does not exceed a measure of quality of the search results for the plurality of entities by a specified threshold value.

The method can further include: generating one or more attribute suggestions for the search query, each attribute suggestion identifying an additional attribute associated with first entity type. Generating the one or more attribute suggestions can include: identifying one or more associated attributes for each of the selected entities; and selecting the associated attributes that maximally refine the selected entities as being attribute suggestions. The method can further include: in response to a user input indicating that a first attribute suggestion matches the first search query, generating an additional search query that includes the first search query and the first attribute suggestion. The method can further include: in response to a user input indicating that a first attribute suggestion does not match the first search query, generating an additional search query that includes the first search query, the first attribute suggestion, and an operator that indicates that resources including the first attribute suggestion should not be included in search results generated for the additional search query.

In general, another innovative aspect of the subject matter described in this specification can be embodied in methods that include the actions of determining that a first search query includes a respective text reference to each of one or more predetermined attributes, wherein each attribute is associated with a first entity type; for each of a plurality of entities of the first entity type, generating a combined search query that includes the first search query and a name of the entity; obtaining search results for each of the plurality of entities using the combined search query for each respective entity; and using the obtained search results to generate combined search results to include in a response to the first search query.

Other embodiments of this aspect include corresponding systems, apparatus, and computer programs encoded on computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

These and other embodiments can each optionally include one or more of the following features. Determining that the first search query includes a respective text reference to each of one or more predetermined attributes can include: determining, only from text of the search query, that the first search query includes a respective text reference to each of one or more predetermined attributes. The method can further include: receiving the first search query from a user device; and providing the combined search results to the user device for presentation in a user interface. The combined search results can be provided in place of search results obtained for the first search query. Determining that the first search query includes a reference to one or more attributes associated with a first entity type can include: determining that at least one term in the first search query appears in an attribute data store. The attribute data store can contain terms from previously submitted queries determined to relate to entities of the first entity type by a query classifier. Using the obtained search results to generate combined search results to include in a response to the first search query can include: generating combined scores for a plurality of resources identified by the obtained search results; and ranking the obtained search results based on the combined scores for the respective resources identified by each search result. The combined score for a particular resource can be a combination of scores assigned to the particular resource by a search engine in response to each of the combined queries. Using the obtained search results to generate combined search results to include in a response to the first search query can include: ranking the obtained search results according to respective scores assigned to the respective resources identified by the search results by a search engine.

The method can further include: determining that, for a particular combined search result obtained in response to a particular combined query, a number of combined search results ranked higher than the particular combined search result in a ranking of the combined search results and obtained in response to the particular query exceeds a specified threshold number; and demoting the particular search result in the ranking of combined search results.

In general, another innovative aspect of the subject matter described in this specification can be embodied in methods that include the actions of determining that a first search query includes a respective text reference to each of one or more predetermined attributes, wherein each attribute is associated with a first entity type; generating a second search query including the first search query and one or more terms that refer to the first entity type; and evaluating search results obtained for the second search query to select one or more names of entities of the first entity type to include in a response to the first search query. Other embodiments of this aspect include corresponding systems, apparatus, and computer programs encoded on computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

These and other embodiments can each optionally include one or more of the following features. The one or more terms that refer to the first entity type can include one or more terms that name the first entity type. Determining that the first search query includes a respective text reference to each of one or more predetermined attributes can include: determining, only from text of the search query, that the first search query includes a respective text reference to each of one or more predetermined attributes. Receiving the first search query from a user device; and providing the selected names to the user device for presentation in a user interface, wherein the selected names are presented separately from search results for the first search query.

The method can further include: identifying resources that include one or more references to entities of the first entity type; and annotating each of the identified resources with an annotation in an index database to indicate that the resource includes one or more references to entities of the first entity type. Evaluating search results obtained for the second search query can include: identifying occurrences of references to entities of the first entity type in resources identified by the search results; and selecting names of entities of the first type that occur most frequently in a same resource identified by the search results as one or more terms in the first search query to be included in a response to the first search query. Determining that the first search query includes a respective text reference to each of one or more attributes associated with entities of the first entity type can include: determining that at least one term in the first search query appears in an attribute data store. The attribute data store can contain terms from previously submitted queries determined to relate to entities of the first entity type by a query classifier.

The method can further include: generating one or more attribute suggestions for the search query, each attribute suggestion identifying an additional attribute associated with first entity type. Generating the one or more attribute suggestions can include: identifying one or more associated attributes for each of the selected entities; and selecting the associated attributes that maximally refine the selected entities as being attribute suggestions. The method can further include: analyzing contents of each resource of a plurality of resources identified by the search results to identify references to attributes associated with entities of the particular type in the contents of the resource. Generating the one or more attribute suggestions can include: identifying a respective number of references to each attribute in the plurality of resources; ranking the attributes based at least in part on the respective numbers of references; and selecting one or more attributes as being attribute suggestions based on the ranking.

The method can further include: identifying respective associated entities and respective associated attributes that are associated with each of the attributes; determining that a total number of associated entities and a total number of associated attributes associated with both a first attribute and a second, lower-ranked attribute exceeds a specified threshold value; and demoting the second, lower-ranked attribute in the ranking.

The method can further include: in response to a user input indicating that a first attribute suggestion matches the first search query, generating an additional search query that includes the first search query and the first attribute suggestion. The method can further include: in response to a user input indicating that a first attribute suggestion does not match the first search query, generating an additional search query that includes the first search query, the first attribute suggestion, and an operator that indicates that resources including the first attribute suggestion should not be included in search results generated for the additional search query.

In general, another innovative aspect of the subject matter described in this specification can be embodied in methods that include the actions of determining that a first search query includes a respective text reference to each of one or more predetermined attributes, wherein each attribute is associated with a first entity type; obtaining search results for the first search query from a search engine, the search results identifying a plurality of resources; identifying entities of the first entity type that are related to any of the plurality of resources identified by the search results; and selecting names of one or more of the identified entities of the first entity type to include in a response to the first search query. Other embodiments of this aspect include corresponding systems, apparatus, and computer programs encoded on computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

These and other embodiments can each optionally include one or more of the following features. Determining that the first search query includes a respective text reference to each of one or more predetermined attributes can include: determining, only from text of the search query, that the first search query includes a respective text reference to each of one or more predetermined attributes. The method can further include: analyzing contents of each of a plurality of resources to identify entities of a first type that are related to the resource; and annotating each of the resources in an index database with annotations identifying the entities that are related to the resource.

Analyzing contents of each of the plurality of resources to identify entities of the first type that are related to the resource can include: identifying occurrences of names of entities in the contents of the resource; and determining that each entity whose name occurs in the resource more than a threshold number of occurrences is related to the resource. Identifying occurrences of names of a particular entity in the contents of the resource can include: determining that one or more occurrences of a name of an entity in the contents of the resource do not relate to the entity. The entities of the first entity type that are related to any of the resources identified by the search results for the first search query can be identified using the annotations.

Evaluating the search results to select names of one or more identified entities of the first type can include: ranking each identified entity based on a respective number of resources identified by the search results to which the entities are related; and selecting the names to be included in the response to the first search query based on the ranking.

The method can further include: for each selected entity name, obtaining search results for a search query including the selected entity name; and including one or more search results obtained for one or more of the search queries including the respective selected entity names with the obtained search results for the first search query in the response to the first search query. The method can further include: promoting one or more search results that identify resources that are related to one or more of the selected entity names in a ranking of the obtained search results.

The method can further include: generating one or more attribute suggestions for the search query, each attribute suggestion identifying an additional attribute associated with first entity type. Generating the one or more attribute suggestions can include: identifying one or more associated attributes for each of the selected entities; and selecting the associated attributes that maximally refine the selected entities as being attribute suggestions. The method can further include: analyzing contents of each resource of a plurality of resources identified by the search results to identify references to attributes associated with entities of the particular type in the contents of the resource. Generating the one or more attribute suggestions can include: identifying a respective number of references to each attribute in the plurality of resources; ranking the attributes based at least in part on the respective numbers of references; and selecting one or more attributes as being attribute suggestions based on the ranking.

The method can further include: identifying respective associated entities and respective associated attributes that are associated with each of the attributes; determining that a total number of associated entities and a total number of associated attributes associated with both a first attribute and a second, lower-ranked attribute exceeds a specified threshold value; and demoting the second, lower-ranked attribute in the ranking.

The method can further include: in response to a user input indicating that a first attribute suggestion matches the first search query, generating an additional search query that includes the first search query and the first attribute suggestion. The method can further include: in response to a user input indicating that a first attribute suggestion does not match the first search query, generating an additional search query that includes the first search query, the first attribute suggestion, and an operator that indicates that resources including the first attribute suggestion should not be included in search results generated for the additional search query.

In general, another innovative aspect of the subject matter described in this specification can be embodied in methods that include the actions of determining that a first search query includes a respective text reference to each of one or more predetermined attributes, wherein each attribute is associated with a first entity type; obtaining search results for the first search query from a search engine, each search result identifying a respective resource; for each of a plurality of the obtained search results, determining an initial score for each of a plurality of entities of the first entity type based on occurrences of names of the entity in the resource identified by the search result; generating a final score for each of the plurality of entities based on the initial scores; and selecting one or more names of entities of the first entity type to include in a response to the first search query based on the final scores. Other embodiments of this aspect include corresponding systems, apparatus, and computer programs encoded on computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

These and other embodiments can each optionally include one or more of the following features. Determining that the first search query includes a respective text reference to each of one or more predetermined attributes can include: determining, only from text of the first search query, that the first search query includes a respective text reference to each of one or more predetermined attributes. Determining that the first search query includes a respective text reference to each of one or more attributes associated with the first entity type can include: determining that at least one term in the first search query appears in an attribute data store. The attribute data store can contain terms from previously submitted queries determined to relate to entities of the first entity type by a query classifier.

The method can further include analyzing contents of each resource identified by the plurality of search results to identify occurrences of names of entities of the first entity type in the contents of the resource. Identifying occurrences of names of a particular entity in the contents of the resource can include: determining that one or more occurrences of a name of an entity in the contents of the resource do not relate to the entity. The initial score for a particular entity for a particular search result can be computed based on a ranking of the particular search result and a number of occurrences of the name of the particular entity in the resource identified by the particular search result.

The initial score for a particular entity for a particular search result can be computed based on a score assigned to the resource identified by the particular search result and a number of occurrences of the name of the particular entity in the resource identified by the particular search result. Generating a final score for each of the entities based on the initial scores can include: for each entity, combining the initial scores for the entity to generate the final score for the entity. The method can further include: normalizing the final scores for each of the plurality of entities based on a respective inverse document frequency of a name of each of the entities.

The method can further include: generating one or more attribute suggestions for the search query, each attribute suggestion identifying an additional attribute associated with first entity type. Generating the one or more attribute suggestions can include: identifying one or more associated attributes for each of the selected entities; and selecting the associated attributes that maximally refine the selected entities as being attribute suggestions. The method can further include: analyzing contents of each resource of a plurality of resources identified by the search results to identify references to attributes associated with entities of the particular type in the contents of the resource. Generating the one or more attribute suggestions can include: identifying a respective number of references to each attribute in the plurality of resources; ranking the attributes based at least in part on the respective numbers of references; and selecting one or more attributes as being attribute suggestions based on the ranking.

The method can further include: identifying respective associated entities and respective associated attributes that are associated with each of the attributes; determining that a total number of associated entities and a total number of associated attributes associated with both a first attribute and a second, lower-ranked attribute exceeds a specified threshold value; and demoting the second, lower-ranked attribute in the ranking.

The method can further include: in response to a user input indicating that a first attribute suggestion matches the first search query, generating an additional search query that includes the first search query and the first attribute suggestion. The method can further include: in response to a user input indicating that a first attribute suggestion does not match the first search query, generating an additional search query that includes the first search query, the first attribute suggestion, and an operator that indicates that resources including the first attribute suggestion should not be included in search results generated for the additional search query.

Particular embodiments of the subject matter described in this specification can be implemented so as to realize one or more of the following advantages. Users can identify the entities that match certain queries using a search engine. In particular, users can effectively identify the medical conditions that are associated with their symptoms by submitting their symptoms to a search system in the form of a search query. Suggestions of additional symptoms related to a received search query that includes a reference to one or more symptoms can be provided to allow a user to refine the medical conditions and, optionally, the search results that are identified in response to the search query. Additionally, the quality of the search results returned in response to certain queries can be improved.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

Figure 1:
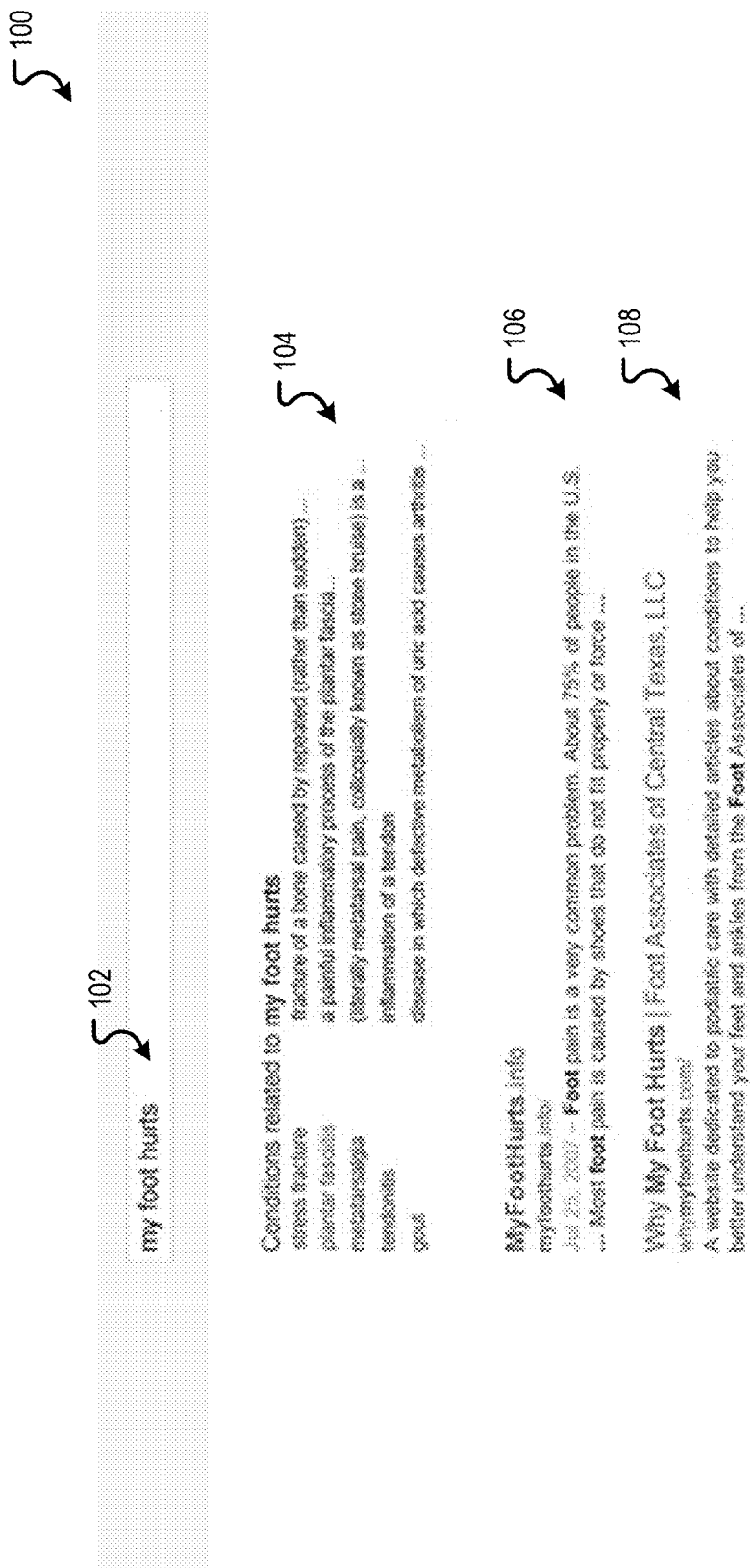
FIG. 1 shows an example search results page.

FIG. 1 shows an example search results page 100 for a search query 102 "my foot hurts." The search results page 100 includes names of medical conditions 104 and two search results 106 and 108. The names of medical conditions 104 and search results 106 and 108 are generated by a search system in response to the search query 102. The search system identifies the search results 106 and 108, for example, using conventional search techniques. The search system determines that names of medical conditions should be returned in response to the search query 102 and returns the names of medical conditions 104 that are associated with the search query 102 for presentation in the search results page 100. In the illustrated example, the criterion met by the search query 102 may be that it includes one or more terms that have been determined to be symptoms of a medical condition. In response to the search query 102, the search system identifies the names of the medical conditions that are to be returned, e.g., by analyzing search results for the search query 102 or for one or more queries derived from the search query 102. Each of the names of medical conditions 104, e.g., "plantar fasciitis" and "tendonitis," are names of medical conditions that the system has determined match the query "my foot hurts." Each name in the names of medical conditions 104 is presented in the form of a link by which a user can get search results for, e.g., a query consisting of the name or a query including the search query 102 and the name. Each name is presented with a snippet of information about the medical condition.

In some implementations, the search engine also generates one or more suggested symptoms for presentation in a search results page in response to particular search queries.

Figure 2:
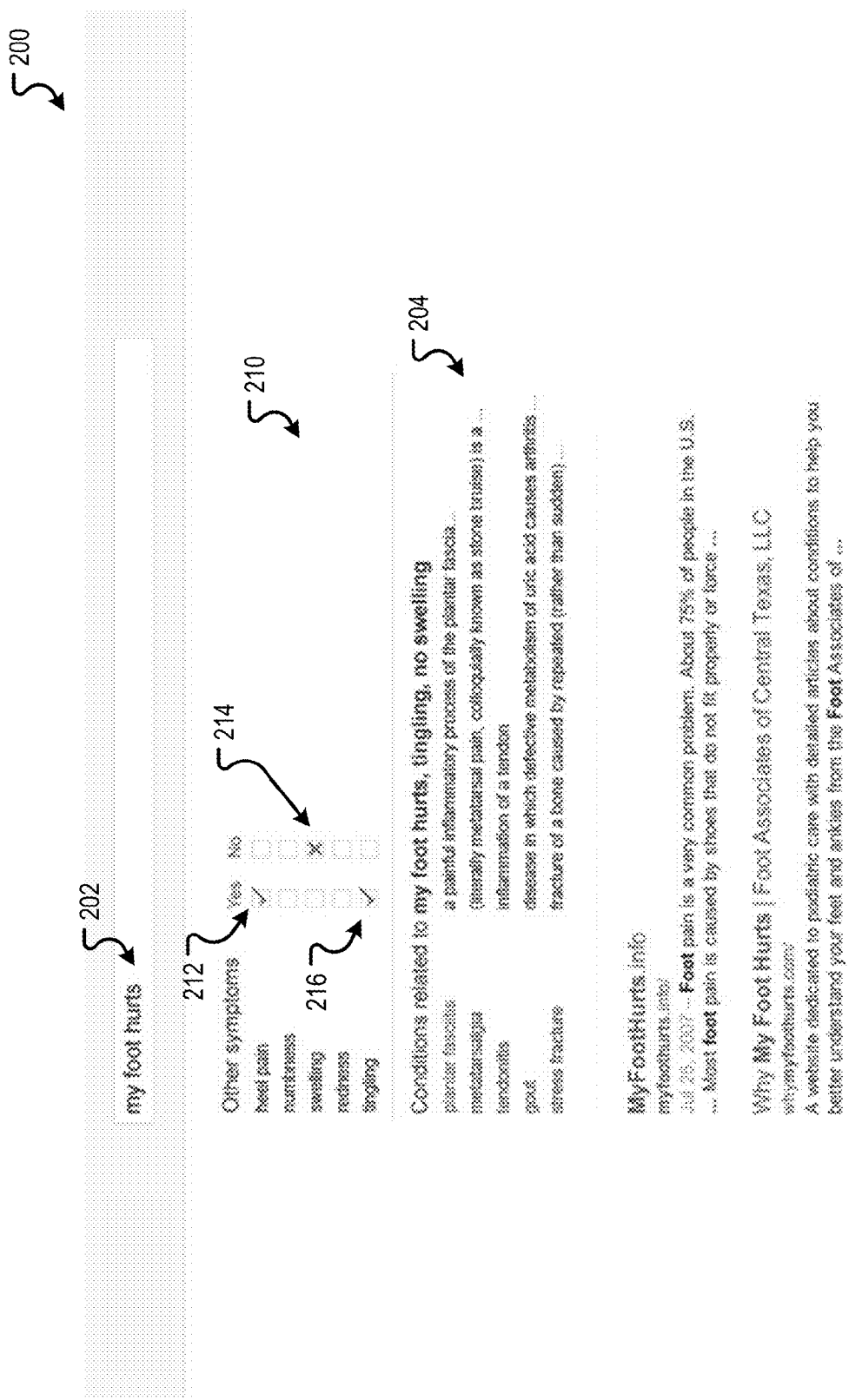
FIG. 2 shows an example search results page that includes symptom suggestions

FIG. 2 shows an example search results page 200 that includes symptom suggestions 210 for the search query 202 "my foot hurts." The search results page 200 also includes names of medical conditions 204. The names of medical conditions 204 and the symptom suggestions 210 are generated by a search system and included in the search results page 200 for presentation, e.g., because the search query 202 includes one or more terms that have been determined to be symptoms of a medical condition. The symptom suggestions 210 are other symptoms that the search system has determined are associated with the search query 202, the names of medical conditions 204, or both. Each of the symptom suggestions 210 is presented with corresponding "yes" and "no" user interface elements. In the illustrated example, the "yes" and "no" user interface elements are checkboxes and the user has selected a "yes" checkbox 212 that corresponds to a symptom suggestion "heel pain," a "no" checkbox 214 that corresponds to a symptom suggestion "swelling," and a "yes" checkbox 216 that corresponds to a symptom suggestion "tingling." In response, a new query has been generated that indicates that the symptoms "heel pain" and "tingling" match the user's query but that the symptom "swelling" does not, e.g., because the user is experiencing heel pain and tingling, but is not experiencing swelling. The new query can append the newly selected symptoms to the original query using Boolean operators. For example, the new query may be "my foot hurts AND heel pain AND tingling NOT swelling." In response to the new query, the names of medical conditions 204 that are displayed have been adjusted. In particular, the name of the medical condition "stress fracture" has been moved to the bottom of the displayed names, i.e., because it is less likely that a user has a stress fracture given the newly identified symptoms that the user is or is not experiencing. In other circumstances, a user selection of a "yes" or "no" user interface element, e.g., can cause new names of medical conditions to be displayed, more or fewer names of medical conditions to be displayed, or different search results to be displayed.

Figure 3:
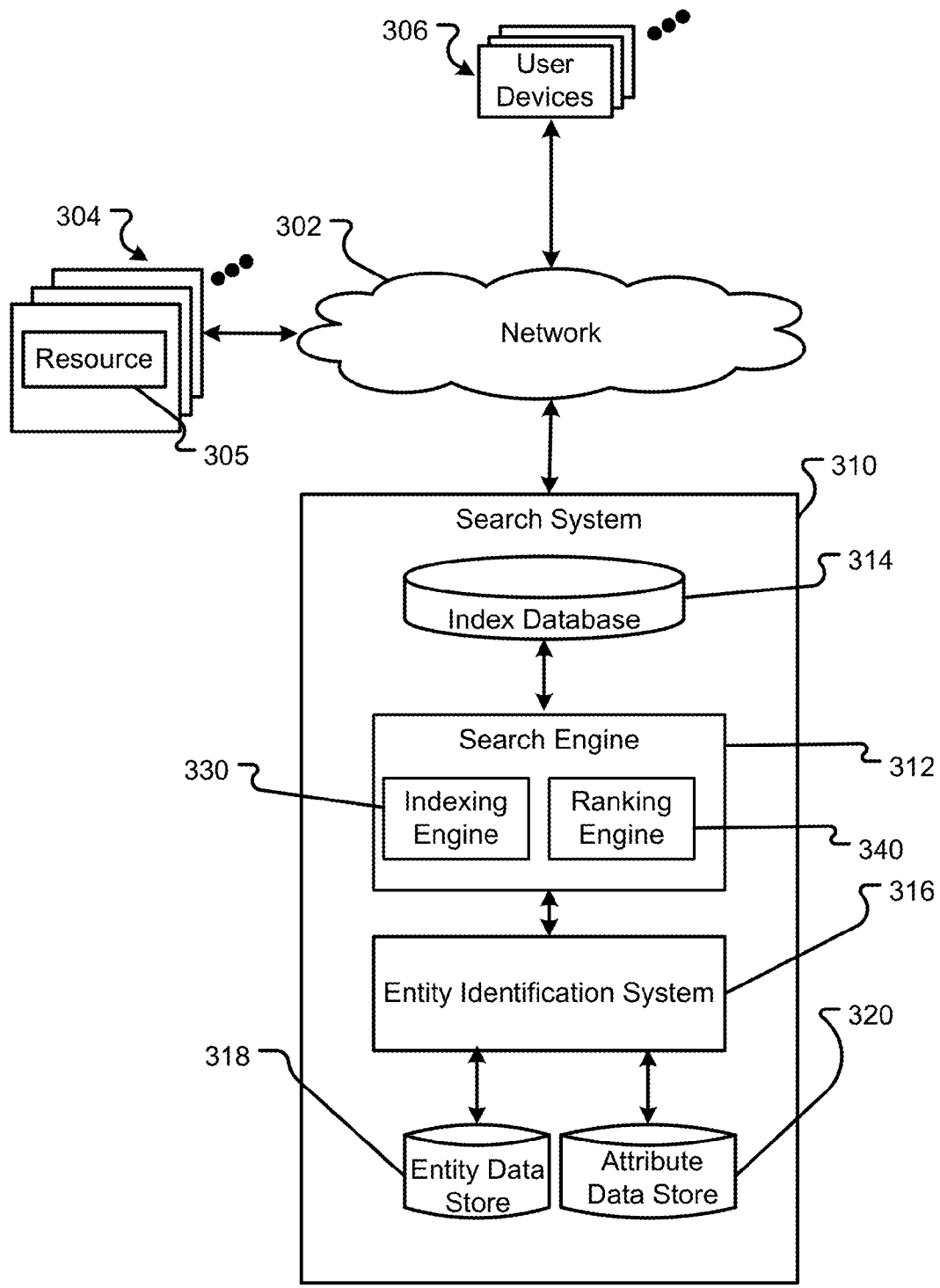
FIG. 3 is a block diagram showing an example search system.

FIG. 3 is a block diagram showing an example search system 310. A network 302, e.g., a local area network (LAN), wide area network (WAN), the Internet, or a combination of them, connects web sites 304, user devices 306, and the search system 310. The search system 310 is implemented on one or more computers in one or more locations and provides search results in response to search queries received from user devices.

The user devices 306 can be personal computers, mobile communication devices, and any other devices that can send and receive data over the network 302. A user device 306 typically includes a software application, e.g., a web agent (browser) or other communication software, to facilitate the sending and receiving of data over the network 302 to and from the search system.

Resources 305 are provided by web sites 304 over the network 302 and are each associated with a resource address. Resources 305 can include, for example, Hypertext Markup Language (HTML) pages, word processing documents, portable document format (PDF) documents, images, video, and feed sources. The resources can include content, such as words, phrases, pictures, and so on, and may include embedded information (such as meta information and hyperlinks) and embedded instructions (such as JavaScript scripts).

The search system 310 includes a search engine 312. The search engine 312 includes an indexing engine 330 that crawls the web sites 304 and indexes the resources provided by the web sites. The index information is stored in an index database 314. In general, the index database 314 can include various types of indexes for resources, including keyword-based indexes, location-based indexes, and other indexes. The search engine 312 also includes a ranking engine 340 that ranks resources, e.g., by quality, by relevancy to a query, or both.

In response to search queries received from user devices 306, the search engine 312 uses the index database 314 to identify resources that match the queries. The search engine 312 generates search results that each identify a respective resource. A search result identifies a resource and includes a link to the resource. Generally, the link is a uniform resource identifier (URL). When the resource is a web page, the search result can include a web page title, a snippet of text extracted from the web page, and the URL of the web page.

The search engine 312 ranks the search results, i.e., places the search results in an order, using the ranking engine 340. After the search results are ranked, the search engine 312 provides the search results to a user device in response to the query ordered according to the ranking, e.g., in one or more search results web pages.

Once a user device receives the search results pages, the user device renders the pages for presentation, generally on a display that is part of or attached to the user device. In response to the user selecting a link in a search result at a user device, the user device requests the resource identified by the resource locator included in the selected search result. The web site hosting the resource receives the request for the resource from the user device and provides the resource to the requesting user device.

The search system 310 also includes or can communicate with an entity identification system 316, which can be implemented on one or more computers in one or more locations. The entity identification system 316 provides names of entities stored in an entity data store 318 for inclusion in responses to certain queries, e.g., queries that include one or more terms stored in an attribute data store 320. Identifying entities will be described in more detail below.

For the sake of clarity, the following description will describe implementations where entities that are medical conditions are identified using queries that include a reference to one or more medical symptoms. However, the entity identification system 316, the attribute data store 318, and the entity data store 320 can also be used to identify entities of other types in response to particular queries.

The attribute data store 320 contains a whitelist of terms that have been determined to be references to or names of medical symptoms. For example, the attribute data store 320 can include terms that are predominately used when referring to medical conditions, e.g., "headache," "runny nose," "infection," and so on.

In some implementations, additional terms can be added to the attribute data store 320 by an off-line query classifier that has been trained using conventional machine learning techniques to analyze queries that have previously been submitted to the search engine 312, e.g., queries that are stored in a query log maintained by the search engine 312, to determine which of the previously submitted queries should be added to the attribute data store 320.

The query classifier can be trained to determine whether each resource of a collection of resources, e.g., some or all of the resources that are indexed in index database 314 or a collection of electronic health records, is likely to be related to medical conditions. For example, the classifier can be trained to recognize medical condition-related terminology in the resource locators (URLs) of resources and determine that resources having at least one medical condition-related term in their resource locator are related to medical conditions. Medical condition-related terminology can include, for example, names of medical conditions, names of symptoms, names of medications, and so on.

The query classifier can then add terms from previously submitted queries that appear in resources that are likely to be related to medical conditions to the attribute data store 320. For instance, if terms in a previously submitted query appear more frequently in resources that relate to medical conditions than in resources that do not relate to medical conditions, the query classifier can add those terms to the attribute data store 320. In some implementations, the query classifier adds the entire query that contains the terms to the attribute data store 320. Alternatively or additionally, the query classifier can be trained to add terms from previously submitted queries that appear in more than a threshold proportion of resources related to medical conditions or that appear in a larger proportion of resources related to medical conditions than in resources that do not relate to medical conditions to the attribute data store 320.

In some implementations, the query classifier is also trained to analyze search results for the previously submitted queries. In these cases, the query classifier determines whether resources identified by search results for a particular previously submitted query are predominately related to medical conditions. For instance, if search results for a previously submitted query include a sufficiently large proportion of search results that identify medical condition-related resources, e.g., if the proportion of search results or high ranking search results identifying medical condition-related resources exceeds a specified threshold value, the query classifier determines that names of medical conditions should be returned in responses to future submissions of the query and adds the query or one or more terms from the query to the attribute data store 320.

The names of medical conditions are stored in an entity data store 318. For a particular medical condition, the entity data store 318 can include the scientific name of the medical condition, e.g., "amyotrophic lateral sclerosis," common names for the medical condition, e.g., "ALS" or "Lou Gehrig's Medical condition," or both.

Figure 4:
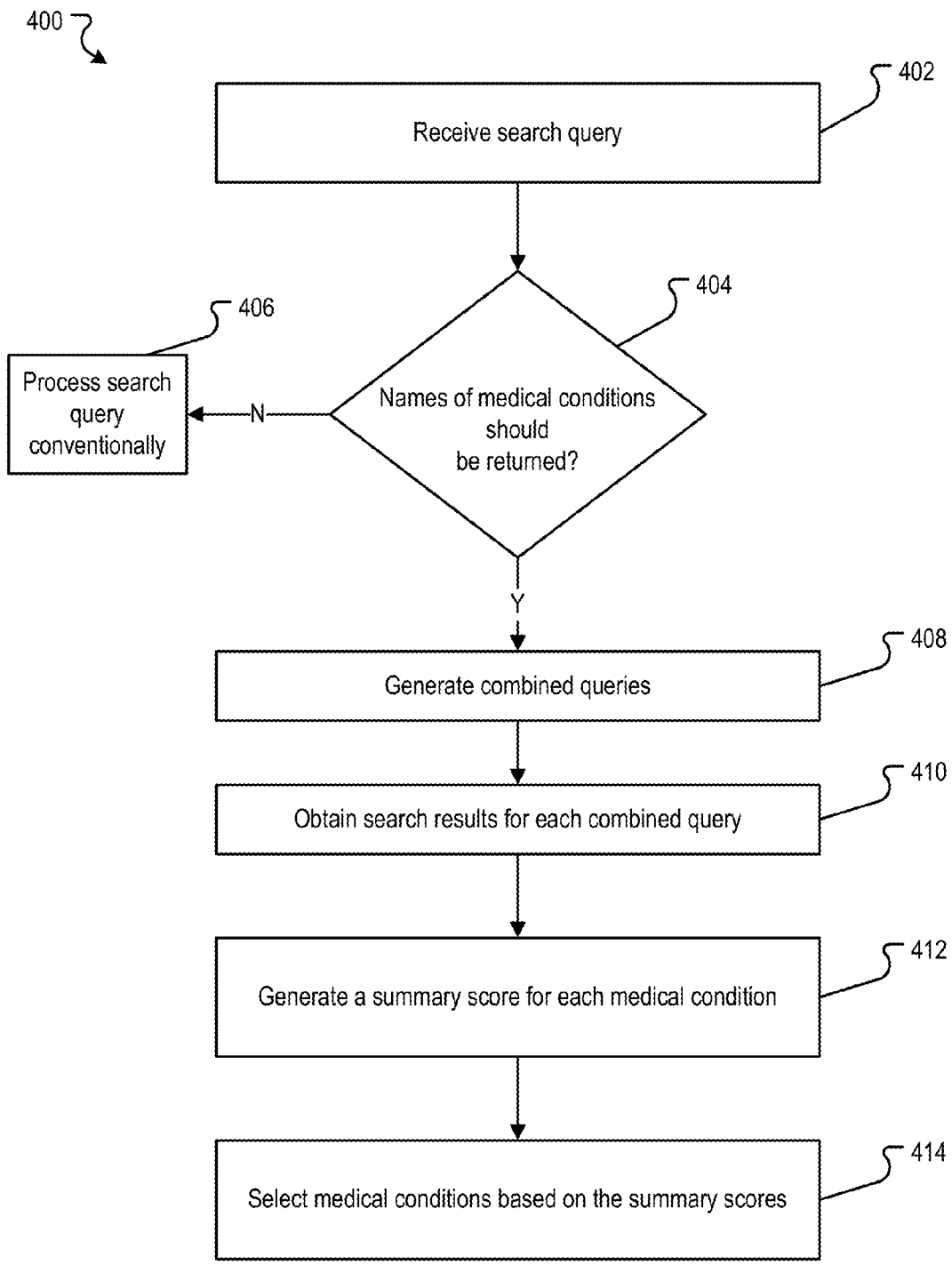
FIG. 4 is a flow diagram of an example process for selecting names of medical conditions that match a received search query using search results.

FIG. 4 is a flow diagram of an example process 400 for selecting names of medical conditions that match a received search query using search results. The process 400 can be performed by a system of one or more computers. For example, a search system, e.g., the search system 310 of FIG. 3, can be used to perform the process 400. The process 400 can be used to identify entities of various types, but is described below with reference to medical conditions.

The system receives a search query from a user device (step 402). The system determines whether names of medical conditions should be returned in response to the query (step 404). For example, the system can determine that it is likely, based on the query submitted by a user, that the user was attempting to find the medical conditions that best match the symptoms the user is currently experiencing and therefore determine that names of medical conditions should be returned in response to the user's query. To make this determination, the system can consult an attribute data store, e.g., the attribute data store 340 of FIG. 3, that stores terms that are likely to be medical symptoms to determine if terms from the search query appear in the attribute data store. If the query consists entirely of terms that appear in the attribute data store, the system determines that names of medical conditions should be returned in response to the query.

In some implementations, if the query does not consist entirely of terms from the query data store, but does include one or more of the terms in the attribute data store, the system can still determine that names of medical conditions are to be returned for the query. For example, if the attribute data store contains the terms "runny nose" and "vomiting" and the system receives a query [I have a runny nose and I am vomiting], with the received query being the text between the [and] symbols, the system initially consults the attribute data store. Even if the query [I have a runny nose and I am vomiting] is not stored in the attribute data store, the system determines that the query includes "runny nose" and "vomiting" (i.e., two of the terms in the attribute data store) and therefore determines that medical conditions should still be returned in response to the query.

Other factors can be considered when determining whether names of medical conditions should be returned. For example, if the query includes one or more terms stored in the attribute data store but also includes the name of a medical condition, the system can determine that names of medical conditions should not be returned, e.g., because it is less likely that a user desires additional medical conditions given that the user has already included a name of a particular medical condition in their query.

The system can also maintain a blacklist of terms or phrases for which medical conditions should not be returned, even though the query includes one or more terms from the attribute data store. If a received query includes one or more terms or phrases in the blacklist, the system can determine that names of medical conditions should not be returned. For example, the phrase "you give me fever" may be included in the blacklist. While this phrase includes a reference to a medical symptom ("fever"), it is a lyric from a popular song and a user submitting a query including the phrase is not likely to be seeking names of medical conditions that match that query. Thus, when the system consults the blacklist for a query that includes the phrase "you give me fever," the system determines not to return names of medical conditions for the query even if the attribute data store includes the term "fever."

In some implementations, instead of or in addition to consulting the attribute data store, the system analyzes search results for the search query obtained from a search engine, e.g., search engine 312 of FIG. 3. If the number of search results that identify a medical condition-related resource exceeds a specified value, the system determines that names of medical conditions should be returned in response to the query. Medical condition-related resources can be identified by an off-line classifier as described above with reference to FIG. 3. Once a resource has been identified as being related to medical conditions, the system can associate data with the resource that indicates that the resource is related to medical conditions. For example, the system can annotate each identified resource in an index, e.g., index database 314 of FIG. 3 or a separate index maintained by the search system. When search results for the query are obtained, the system can consult the index to determine whether the number of search results that identify a medical condition-related resource exceeds the specified value. Alternatively, the system can determine whether the proportion of highest-ranked search results (e.g., the ten, fifty, or one hundred highest-ranked search results) that identify medical condition-related resources exceeds a specified threshold value.

If the system determines that names of medical conditions should not be returned as separate items in a response to the query, the system processes the search query conventionally (step 406). For example, the system can obtain search results in response to the query from a search engine and transmit the search results to the user device in one or more search results pages without separately including any medical condition names.

If the system determines that names of medical conditions should be returned, the system generates a combined query for each medical condition of a set of medical conditions (step 408). The system uses names of medical conditions stored in an entity data store, e.g., the entity data store 318 of FIG. 3, to generate the combined queries, so that each combined query includes the received query and the name of a medical condition in the entity data store. For example, if the received query is [why am I so tired], the system will generate queries that combine "why am I so tired" with names of medical conditions stored in the entity data store, e.g., [why am I so tired "Aarskog Syndrome"], [why am I so tired "Aase Syndrome"], [why am I so tired "Abdominal Aortic Aneurysm"], and so on. In some implementations, the combined queries can include additional terms, such as Boolean operators. The combined queries can also include more than one medical condition name. If, for example, the entity data store contains the common name and scientific name for a medical condition, the combined query could include both the common name and the scientific name instead of generating a separate combined query for each since the two names are synonyms. The synonyms can be included in the combined search query using, for example, a Boolean "OR" operator.

In some implementations, the system generates a combined query for each medical condition in the entity data store. Alternatively, combined queries are only generated for a portion of the medical conditions in the entity data store. For example, the system can consult a data store that stores associations between medical conditions and symptoms or sets of symptoms characteristic of each medical condition. When a query is received that includes one or more references to medical symptoms, the system can filter the medical condition names included in the entity data store so that combined queries are generated only for medical conditions that are associated with at least one symptom referred to in the query. For example, the medical condition names can be ranked according to the number of symptoms referenced in the query that are associated with the medical condition, and combined queries can be generated only for highly-ranked medical condition names. The associations can be produced by, for example, a co-occurrence analysis of medical conditions and symptoms in the collection of resources or in previously submitted queries, or by use of pre-generated health-specific structured data.

The system obtains search results for each combined query (step 410). The system generates a summary score for each medical condition based on search results obtained for the combined query (step 412). As described above with reference to FIG. 3, each obtained search result is associated with a score determined by the search engine for the resource identified by the search result. The system uses these scores to generate summary scores for each combined search query. The summary score for a particular combined query is a function of the scores associated with search results for the combined query. In some implementations, only a specified number, e.g., ten, fifty, or one hundred, of highest-scoring search results for each combined query are used to generate the summary scores. Depending on the implementation, fewer or more scores can be used.

The summary score for a combined query can be, for example, the sum of the scores associated with search results for the combined query. Other functions could be used in order to, for example, reduce the influence of a few very high-scoring resources. For instance, the summary score can be the arithmetic or harmonic mean or other central tendency of the scores associated with the obtained search results. The summary scores can also be a sum of the logarithm of each score, the geometric mean of all or some of the scores, and so on.

Additionally, once the summary scores for each combined query have been generated, the system can normalize each summary score. Because the names of certain medical conditions can appear more often in resources than the names of other medical conditions, the summary scores for those common medical conditions may be undesirably inflated in relation to other medical conditions that may better match a received query. The system can normalize the summary scores to reduce this effect. For instance, each summary score may be adjusted based on the inverse document frequency of the names of its respective medical condition.

The system selects medical conditions based on the summary scores (step 414). The system orders the medical conditions according to their summary scores and selects the medical conditions based on the order. The system can select, for example, a specified number of medical conditions having the highest scores or all of the medical conditions having a summary score that exceeds a specified threshold. In some implementations, the system selects all of the medical conditions having a summary score exceeding the specified threshold, so long as the number of selected medical conditions does not exceed the specified number of medical conditions.

Once the medical conditions are selected, the system can provide the names, e.g., the common name, the scientific name, or both, of the selected medical conditions to a search engine for inclusion in a search results page that is transmitted to a user device for presentation in a user interface. Alternatively, the names of the selected medical conditions can be transmitted to the user device for presentation in a user interface in place of a search results page. Each name can be presented, for example, in the form of a link by which a user can get search results for a query consisting of the name. The links can be ordered according to the scores for the corresponding medical conditions and presented so that links associated with the highest scoring medical conditions are more prominently displayed.

In some situations, two or more of the selected medical condition names can be grouped together before presentation. For example, names can be grouped together if the names are synonyms for the same medical condition or are a plural and singular form of the same medical condition. In addition, in some implementations, the names of two or more medical conditions can be grouped together if the conditions belong to the same category of medical condition. For example, if "psoriasis" and "eczema" are both selected in response to a query, the system can identify that both "psoriasis" and "eczema" are skin diseases, e.g., using a pre-computed list of entity-category associations, and determine that the two medical conditions should be grouped before presentation to the user. The two conditions can then be presented in the form of a single link, e.g., with associated text "skin diseases (e.g., psoriasis, eczema)." The user can select the link to get search results for, e.g., a query including "skin diseases," "psoriasis AND eczema," or both.

In some implementations, after obtaining the search results for the combined queries, the system may determine not to include any medical condition names in the search results page for an original query. For example, the system can compare the number, quality, or both of search results for the original query with the search results for each of the combined queries. If the difference between the number or quality or both of search results for the original query and the combined queries exceeds a threshold value, the system can determine not to return any medical condition names. That is, if the search results for the original query are sufficiently better in number or quality or both than the search results for the combined query, the system does not return any medical condition names to the user. Alternatively, the system can determine not to return any medical condition names if the number or quality or both of search results for the original query exceed respective threshold values.

In some implementations, the selected medical conditions can be refined based on user interaction. For example, once the names of the selected medical conditions are presented to the user in a user interface, the user may submit a second query that references additional attributes, e.g., additional symptoms the user is experiencing. The system can generate additional combined queries for the second query and select medical conditions with attributes that match the second query. In some implementations, the medical conditions identified for each query can then be combined using a combining function, and names of medical conditions from the combined list can be presented to the user. The combining function can include, for example, filtering the selected medical conditions to include only medical conditions identified for both queries. The combining function can also generate new scores by adding, multiplying, or otherwise combining the respective summary scores for the two queries for each medical condition. The names of the medical conditions having the highest combined scores can then be presented to the user.

While the foregoing description has described determining whether to return names of medical conditions for particular queries and then selecting the names that are to be returned, an entity identification system, e.g., entity identification system 316 of FIG. 3, can also be used to identify entities of other types, such as movies, books, public figures, and so on, which have a corresponding set of names stored in an entity data store, e.g., entity data store 318 of FIG. 3, and corresponding attributes stored in an attribute data store, e.g., attribute data store 320 of FIG. 3.

Figure 5:
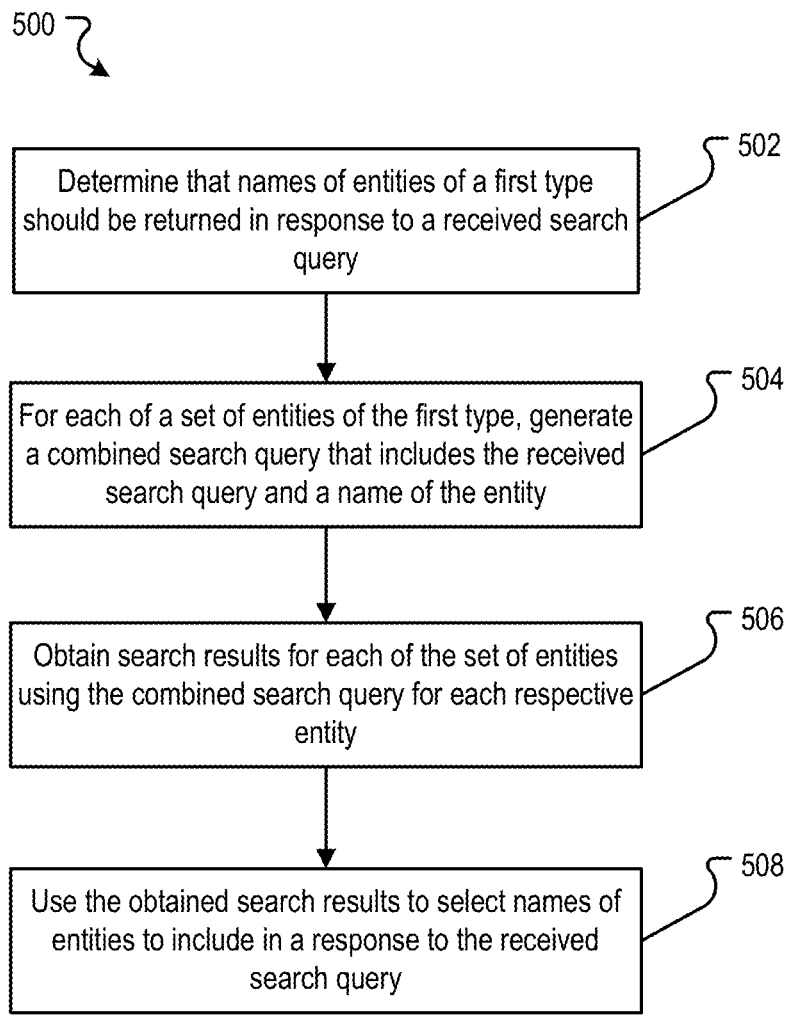
FIG. 5 is a flow diagram of an example process for identifying entities using search results.

FIG. 5 is a flow diagram of an example process 500 for identifying entities using search results. The process 500 can be performed by a system of one or more computers. For example, a search system, e.g., the search system 310 of FIG. 3, can perform the process 500.

The system determines that names of entities of a particular type should be returned in response to a received search query (step 502). The search system can determine that the search query includes one or more references to one or more attributes associated with the entity type, by, for example, determining that the search query includes one or more terms stored in an attribute data store. The attribute data store contains terms that have been determined to be attributes of the entity type. In some implementations, the attribute data store includes previously-submitted queries that have been added to the data store by a classifier trained using machine learning techniques. In some implementations, the system also consults a blacklist of terms and determines that the search query does not include any terms from the blacklist. In addition to or instead of consulting the blacklist, the system can also determine that the search query does not include any names of entities of the type by consulting an entity data store.

In some implementations, instead of or in addition to consulting the attribute data store, the system analyzes search results for the search query obtained from a search engine and determines that the number of search results that identify a resource related to entities of the type exceeds a specified value.

For each of a set of entities of the entity type, the system generates a combined search query that includes the received search query and a name of the entity (step 504). The set of entities of the entity type can consist of every entity of the type for which a name is stored in an entity data store that is accessible by the system. Alternatively, the entities having names stored in the entity data store can be filtered so that the set of entities includes only the entities that are likely to be relevant to the search query.

The system obtains search results for each of the set of entities using the combined search queries (step 506). The system uses the obtained search results to select names of entities to include in a response to the search query (step 508). For example, the system can generate a summary score for each entity that is included in a combined query. The summary scores can be based on scores associated with each search result, e.g., scores for resources identified by the search results that are used to rank the search results. The system can select the entities based on the summary scores.

In some implementations, instead of or in addition to returning names of entities that best match a particular received query, the system can use search results for the combined queries to improve the quality of the search results returned to the user for the received search query.

Figure 6:
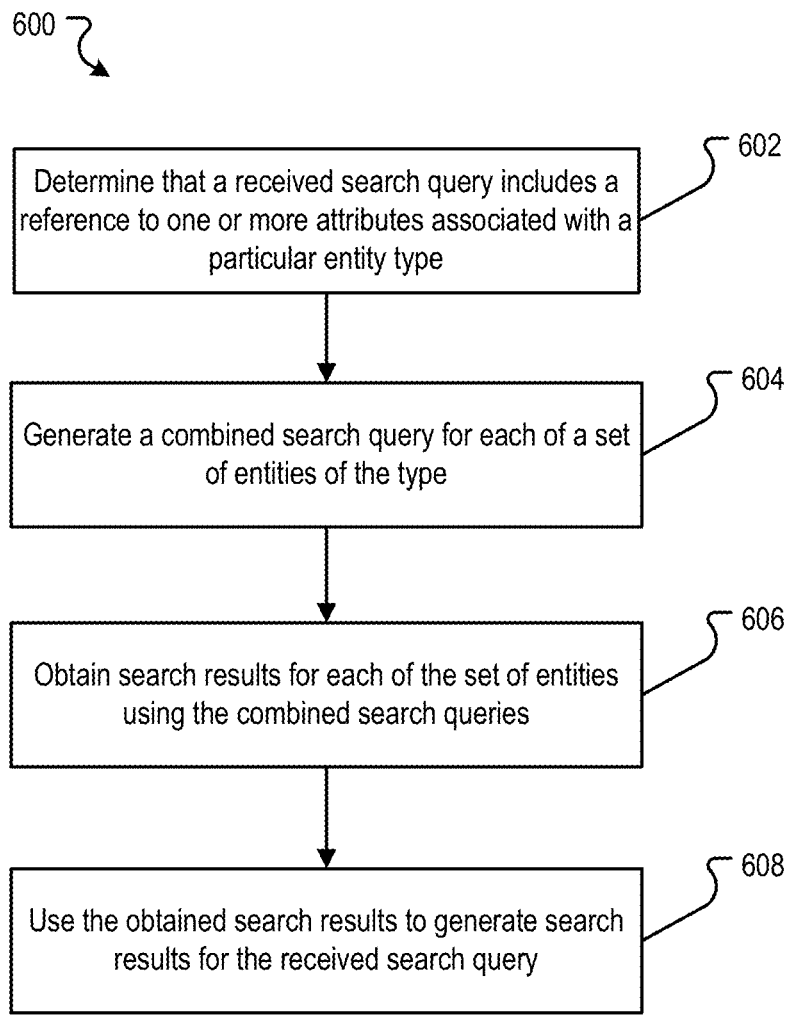
FIG. 6 is a flow diagram of an example process for returning search results in response to a received query.

FIG. 6 is a flow diagram of an example process 600 for returning search results in response to a received search query. The process 600 can be performed by a system one or more computers. For example, a search system, e.g., the search system 310 of FIG. 3, can perform the process 600.

The system determines that a received search query includes one or more references to one or more attributes associated with a particular entity type (step 602). The system can make this determination using any of the techniques described above.

For each of a set of entities of the entity type, the system generates a combined search query that includes the received search query and a name of the entity (step 604).

The system obtains search results for each entity of the set of entities using the combined search query for the entity (step 606) and uses the obtained search results to generate search results for the received search query (step 608). In some implementations, the system generates combined scores for resources identified by search results for the combined queries. The combined score for a particular resource is a function of the score, as determined by the search engine, for each search result that identifies the resource. For example, the combined score can be the maximum, soft maximum, arithmetic mean, or geometric mean of the score of each search result identifying the particular resource obtained in response to the combined queries. The soft maximum of scores $S_1$, $S_2$, $S_3, \ldots, S_N$ is defined as softmax$(S_1, S_2, S_3, \ldots, S_N)$=log(exp $(S_1)$+exp$(S_2)$+exp$(S_3)$+ ... +exp$(S_N)$).

The system then ranks, i.e., places in an order, the obtained search results according to the combined scores for their respective associated resources. Duplicative search results, e.g., search results that identify the same resource as another, higher-ranked search result, can be removed from the order so that resources are not associated with more than one search result in the generated search results. Alternatively, the system can rank the obtained search results for the combined queries according to the scores determined by the search engine for each result, i.e., without modifying the scores assigned to the search result by the search engine by generating a combined score. The system can then remove duplicative search results from the ranking.

In some implementations, after the search results are ranked, the system can demote search results that are drawn from result sets that are already strongly represented by higher-ranked search results. That is, for a particular search result obtained in response to a particular combined query, the system can demote, i.e., move down in the order, the search result if other search results obtained in response to the particular combined query make up more than a specified threshold number or specified threshold proportion of the search results that are above the particular search result in the order.

After the search results are ranked, the system can provide the search results to a user device in response to the received query, ordered according to the ranking. The results can be provided in one or more search results web pages.

Figure 7:
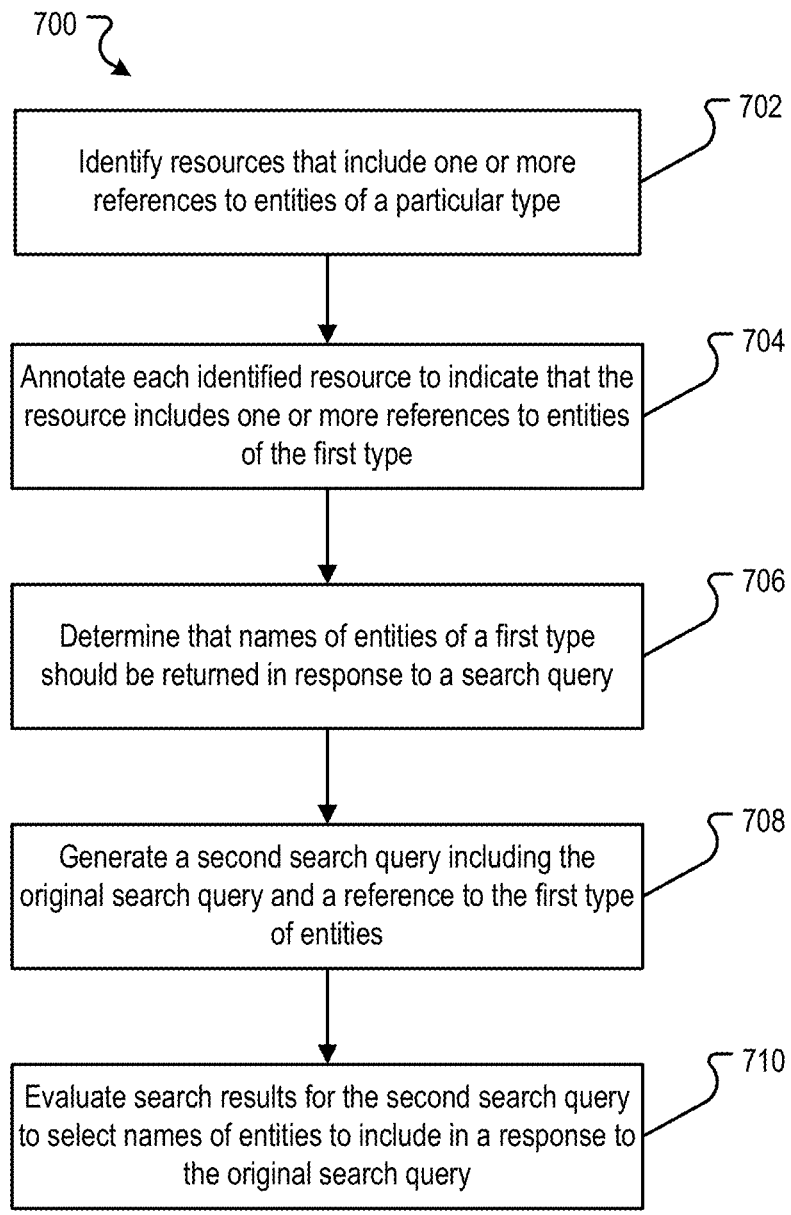
FIG. 7 is a flow diagram of an example process for using annotations in an index database to identify entities.

FIG. 7 is a flow diagram of an example process 700 for using annotations in an index database to identify entities. The process 700 can be performed by a system of one or more computers. For example, a search system, e.g., the search system 310 of FIG. 3, can perform the process 700. The system can perform the process for each of multiple entity types.

The system identifies resources that include one or more references to entities of a particular type (step 702). For example, the particular type can be medical conditions and resources that include one or more references to medical conditions, e.g., names of medical conditions, can be identified by the search system. The collection of resources can be, for example, resources indexed by the search system for use in returning search results in response to search queries. Alternatively, the collection of documents can be specific to the particular type. For example, if the particular type is medical conditions, the collection of documents can be, e.g., a collection of electronic health records.

In some implementations, in the case of entities whose names are unambiguous, i.e., not commonly used in other contexts, the system can identify each occurrence of the name of the entity in the resource as a reference to the entity. However, for entities whose names are potentially ambiguous, e.g., are used in multiple contexts, the system can use conventional named entity recognition techniques to classify the contents of the resource into categories to determine which occurrences of names of entities refer to the entity and which are references to an unrelated context. Named entity recognition is described in more detail in, for example, C. Whitelaw, A. Khelenbeck, N. Petrovic, L. Ungar, *Web-Scale Named Entity Recognition*, Proceedings of the 17th ACM Conference on Information and Knowledge Management, pp. 123-132 (October 2008), and D. Nadeau, S. Sekine, *A Survey of Named Entity Recognition and Classification*, Lingvisticae Investigationes, Volume 30, Number 1, 2007, pp. 3-28(24). The system can then determine that, for an entity whose name is potentially ambiguous, an occurrence of the entity name in the resource is a reference to the resource only if the occurrence refers to the entity and not to an unrelated context.

The system annotates each identified resource in an index database to indicate that the resource includes one or more references to entities of the particular type (step 704). For example, the search system can annotate the resources in the index database 314 of FIG. 3 or a separate index database maintained by the search system.

The system can identify the resources that include references to entities of the particular type and annotate the resources in the index at various times. In some implementations, the system analyzes the contents of resources to determine whether they include references to entities of the particular type at index time. In some other implementations, the search system analyzes the contents of resources independently from the indexing process but before search time. In yet other implementations, the search system analyzes the contents of resources at search time.

The resource can be annotated with, for example, a reference to the particular entity type whenever a reference to an entity of the particular type occurs in the resource. For instance, whenever a name of a medical condition occurs in a resource, the search system can add annotate the resource in the index with a "medical condition" tag.

The system determines that names of entities of the particular type should be returned in response to a search query (step 706). The system can make this determination using any of the techniques described above.

The system generates a second search query that includes the original search query and a reference to the particular type (step 708). For example, the search system can receive a query [heartburn inflammation]. After determining that names of medical conditions should be returned in response to this query, the search system can generate a second query [heartburn inflammation medical condition]. Alternatively, a search operator such as "type" or "topic" can be implemented that takes a name of a type as an argument. For a search query that includes the operator and a reference to the particular type, the search system can limit search results to search results identifying resources that are annotated to indicate that they include one or more references to entities of that type. For the [heartburn inflammation] query, for example, the generated second search query can be [heartburn inflammation topic: medical condition].

The system evaluates search results obtained for the second search query to select names of entities to include in a response to the original search query (step 710). Using the annotations, the system can identify all occurrences of terms in the search query in the same resource as a name of an entity of the particular type in resources identified by, e.g., all of the search results or a specified number of highest-ranked search results. For example, for the [heartburn inflammation medical condition] query, the system can identify each occurrence of the two symptoms included in the query (in this example, heartburn and inflammation) in the same resource as the name of any medical condition.

The system can then determine that the names of the medical conditions that most frequently occur in the same resource as the terms in the search query should be included in the response to the search query. The system can identify, for example, a specified number of entities having the highest number of associated occurrences or any number of entities having a threshold number of associated occurrences. In some implementations, if none of the entities of the particular type have a number of associated occurrences that exceeds a specified threshold value, the system can determine not to include any names of entities of the particular type in the response to the original search query.

Figure 8:
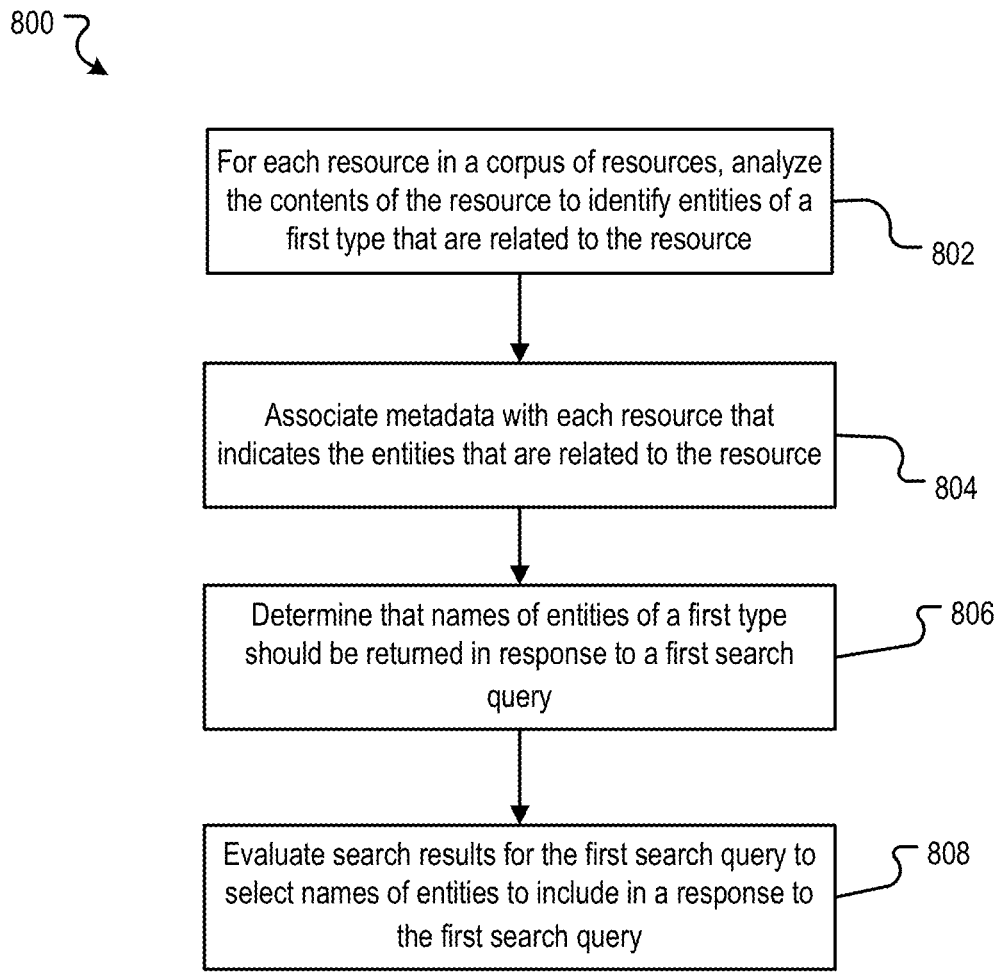
FIG. 8 is a flow diagram of another example process for using annotations in an index database to identify entities.

FIG. 8 is a flow diagram of another example process 800 for using annotations in an index database to identify entities. The process 800 can be performed by a system of one or more computers. For example, a search system, e.g., the search system 310 of FIG. 3, can perform the process 800. The system can perform the process for each of multiple entity types.

For each resource in a collection of resources, the system analyzes the contents of the resource to identify entities of a particular type that are related to the resource (step 802). The collection of resources can be, for example, resources indexed by the search system for use in generating search results in response to search queries. The system can determine that entities whose name occurs in the contents of a resource more than a specified number of times are related to the resource.

In some other implementations, for entities whose names are potentially ambiguous, the system can then determine that the entity is related to a resource only if the number of occurrences that refer to the entity exceeds a specified number, e.g., using named entity recognition techniques as described above with reference to FIG. 7.

The system annotates each identified resource in an index database to identify the entities that are related to the resource (step 804). The system can identify the entities that are related to resources and annotate the resources in the index at various times. In some implementations, the system analyzes the contents of resources at index time to identify entities of a particular type that are associated with the resource. In some other implementations, the search system analyzes the contents of resources independently from the indexing process but before search time. In some other implementations, the search system analyzes the contents of resources at search time. The resources can be annotated with, for example, a tag referencing each entity related to the resource. For instance, if the system determines that a particular resource is related to the medical condition "narcolepsy," the system can annotate the resource with a "narcolepsy" tag in the index.

The system determines that names of entities of the particular type should be returned in response to a received search query (step 806). The system can make this determination using any of the techniques described above.

The system evaluates search results for the search query to select names of entities to include in a response to the search query (step 808). The system can consult the annotations in the index associated with, for example, the resources identified by each of a specified number of highest-scoring search results for the search query to obtain the entities related to each resource. The system can order the entities in an order based on how often each entity is related to a resource and select the names of entities based on the order. For example, the system can select a specified number of names corresponding to the most frequently related entities. In some implementations, if none of the entities of the particular type are related to a sufficient number of resources, the system can determine not to include any names of entities of the particular type in the response to the search query.

For example, for a search query [I have a runny nose and I am vomiting], the system can determine that names of medical conditions should be returned by consulting an attribute data store. The system can obtain search results for the query and consult an index that includes annotations associated with each resource identified by the top twenty, fifty, or one hundred search results obtained for the [I have a runny nose and I am vomiting] query. Using the annotations, the system can determine which medical condition names, e.g., "stomach flu," "viral gastroenteritis," or "common cold," appear most often in the annotations associated with those resources. The system can then select all of the medical condition names appearing more than a specified number of times or a specified number of most-frequently appearing medical condition names.

In some implementations, the system can alter the search results that are returned in response to the search query based on the selected entity names. For example, in addition to obtaining search results for the received search query, the system can also, for each selected entity name, obtain search results for a query consisting of the entity name. The system can then include one or more highly-ranked search results for the queries that include added entity names with the search results for the received search query, e.g., by ranking the combined set of search results according to scores associated with each result by the search engine.

Alternatively, the system can obtain search results for the received search query and promote search results that identify resources that are related to one or more of the selected entity names. For example, the system can obtain search results for a query [top of foot pain]. If "stress fracture" is one of the entity names selected for the query, the system can promote search results that identify resources that are related to the "stress fracture" entity, as indicated by annotations associated with the resources in the index. The system can promote a search result, by for example, increasing the score associated with the search result by the search engine or by moving the search result to a higher place in a ranking of the search results.

Figure 9:
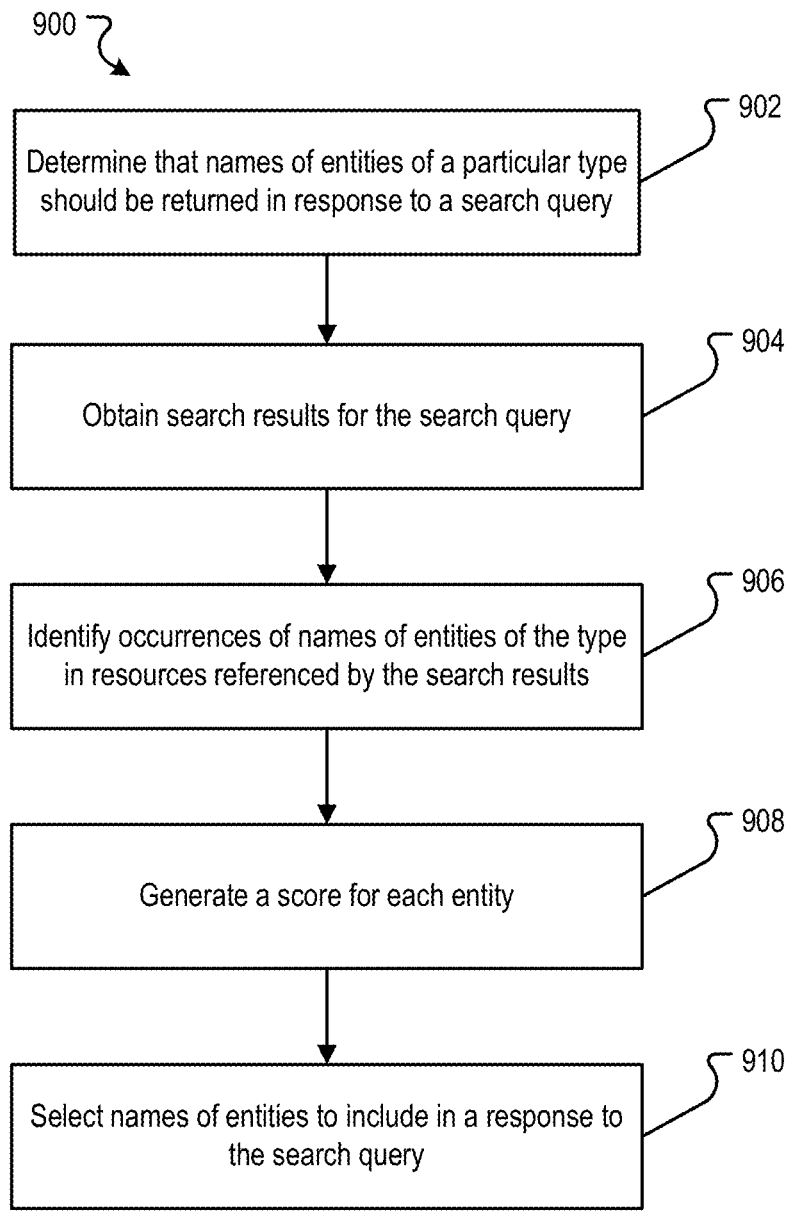
FIG. 9 is a flow diagram of another example process for identifying entities using search results Like reference numbers and designations in the various drawings indicate like elements.

FIG. 9 is a flow diagram of another example process 900 for identifying entities using search results. The process 900 can be performed by a system of one or more computers. For example, a search system, e.g., the search system 310 of FIG. 3, can perform the process 500.

The system determines that names of entities of a particular type should be returned in response to a received search query (step 902). The system can make this determination using any of the techniques described above.

The system obtains search results in response to the search query from a search engine (step 904).

The system identifies occurrences of names of entities of the particular type in resources identified by the search results (step 906). For each resource identified by each search result or each of a specified number of highest-ranked search results, the system identifies a number of occurrences of names of a set of entities of the particular type, e.g., each name of an entity of the particular type that is stored in an entity data store or a subset of the names stored in the entity data store. In some implementations, for names of entities that are potentially ambiguous, the system uses named entity recognition to only count occurrences that refer to the entity as occurrences, e.g., as described above with reference to FIG. 8.

The system can identify the occurrences at various times. In some implementations, the system analyzes the contents of the resources to identify the occurrences at search time, e.g., when the query is received. In some other implementations, the system analyzes the contents of resources at index time to identify the occurrences and annotates the resources in an index to indicate the number of occurrences of each entity in the resource, e.g., as described above. When the query is received, the system can use the annotations to identify the occurrences. In some other implementations, the search system analyzes the contents of resources independently from the indexing process but before search time and annotates the resources in the index accordingly. In some implementations, at the same time as or independently from analyzing the resources to identify occurrence of names of entities of the particular type, the system also identifies occurrences of references to attributes associated with the particular type. The identified occurrences can then be used, e.g., to identify attribute suggestions as will be described in more detail below.

The system then generates a score for each entity (step 908). The scores are calculated based on the identified occurrences and a ranking of the search results. In particular, for a given entity, the system generates an initial score for each result or each of the specified number of highest-ranked search results that is based on the ranking of the search result and the number of occurrences of the entity in the resource identified by the search result. Alternatively, instead of using the ranking of the search result, the system can generate the initial score based on the score associated with the search result by the search engine. The entity scores are generated so that, given the same number of occurrences of an entity in two resources, the score for a resource identified by the higher-ranked search result (or the score for the higher-scoring search result) will be higher than the score for the lower-ranked ranked search result (or the score for the lower-scoring search result).

In some implementations, certain occurrences of a name of an entity in a resource are given more weight in generating the initial score for the entity for the resource than others. For example, occurrences of an entity name in the title of the resource or in metadata associated with the resource can be given an increased weight.

Once the initial scores for the entity have been determined, the system combines the initial scores to generate a combined score for the entity. The combined score for an entity can be, for example, the sum of the initial scores. Other functions can also be used. For instance, the combined score can be the arithmetic or harmonic mean or other central tendency of the initial scores. The initial scores can also be a sum of the logarithm of each initial score, the geometric mean of all or some of the initial scores, and so on.

Additionally, once the combined scores for each entity have been generated, the system can normalize the combined scores. Because the names of certain entities of a given type can appear more often in resources than the names of other entities of the type, the combined scores for those common entities may be undesirably inflated in relation to combined scores for other entities that may better match a received query. The system can normalize the combined scores to reduce this effect. For instance, each combined score may be adjusted based on the inverse document frequency of the name (or names) of its respective entity.

The system selects names of entities to be included in a response to the search query (step 910). The names can be selected based on the combined scores. For example, the system can select the names of a specified number of highest-scoring entities or of each entity whose score exceeds a specified threshold value. In some implementations, if none of the combined scores exceed a specified threshold value or if the number or quality or both of search results for the original query exceed respective threshold values, the system can determine not to return names of entities of the particular type in response to the search query.

In any of the implementations for selecting names of entities of a particular type described above, the system can also generate suggestions to assist a user in refining presented entity names. The suggestions can include additional attributes, e.g., additional symptoms. In some implementations, the additional attributes are attributes that would maximally refine the selected entities and are additional attributes are generated based on a pre-computed list of attribute-entity associations. For example, the system can consult the list of attribute-topic associations to determine the attributes that, if selected by a user, would maximally refine the selected entities. Attributes that maximally refine the selected entities can be the attributes that, if presented to the user as an attribute suggestion and selected by the user, e.g., as described below, would result in the largest change to the names that are displayed to the user.

Alternatively, the system can use identified occurrences of references to attributes in resources identified by the search results for the original query to generate the additional attributes. The occurrences can be identified, e.g., as described above with reference to occurrences of entity names. The system can use the identified occurrences to identify attributes that are associated with the query. For example, for a set of attributes associated with entities of the particular type, the system can rank the attributes based on the total number of occurrences of the attributes in resources identified by a specified number of highest-ranked search results. The system can then select a specified number of highest-ranked attributes as being associated with the query. Alternatively, the system can score the attributes in the same manner as described above for entities of the particular type. The system can then select a specified number of highest-scoring attributes or each attribute having a score above a specified threshold value as being associated with the query. The system can then identify the associated attributes as suggestions for the query.

In some implementations, the system uses a pre-computed list of associations to diversify the additional attributes. For example, the list can identify the entities and other attributes that are associated with each of a set of attributes of the particular type. For each additional attribute, the system identifies the entities and other attributes that are associated with the additional attribute. The system then determines whether the associated entities and other attributes for any two of the additional attributes have an overlap that exceeds a specified threshold, e.g., whether more than a specified threshold number of attributes or entities are associated with both a first and a second additional attribute. If two of the additional attributes have an overlap that exceeds the specified threshold, the system can discard or demote the lower-ranked additional attribute.

For example, for a received query [hurts when I breathe], the system may identify that the three highest-ranked additional symptoms are "cough," "fever," and "sputum," in that order. Using the pre-computed list of associations, the system may find a significant overlap in the conditions and symptoms associated with "cough" and the conditions and symptoms associated with "sputum." The system may then discard "sputum," e.g., replace it in the additional symptoms with a different symptom that is more diverse compared to the other additional symptoms.

In response to a user input selecting one of the presented suggestions, the search system can, e.g., generate an additional query that includes the original query and the selected suggestion. As described above with reference to FIG. 2, in some implementations, each suggestion is presented with corresponding user interface elements that allow a user to indicate that the suggestion matches or does not match their original query. In response to a user input selecting the user interface element that indicates that the suggestion matches the originally query, an additional query can be generated that includes the original query and the selected suggestion separated by, e.g., an "AND" operator. In response to a user input selecting the user interface element that indicates that the suggestion does not match the original query, an additional query can be generated that includes the original query and the selected suggestion separated by an operator that indicates that resources including the selected attribute suggestion should not be included in search results generated for the additional search query, e.g., an "AND NOT," "NOT," or "-" operator.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that data store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any implementation or of what may be claimed, but rather as descriptions of features that may be specific to particular embodiments of particular implementations. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method performed by a system comprising one or more computers, the method comprising:
    determining that a first search query includes a respective text reference to each of one or more predetermined attributes, wherein each attribute is associated with a first entity type;
    for each of a plurality of entities of the first entity type, generating a combined search query that includes the first search query and a name of the entity;
    obtaining search results from a search engine for each of the plurality of entities using the combined search query for each respective entity; and
    using the obtained search results to generate combined search results to include in a response to the first search query, wherein using the obtained search results to generate combined search results comprises:
        generating a respective combined score for each of a plurality of resources identified by the obtained search results, wherein the respective combined score for each resource is a combination of scores associated with obtained search results identifying the resource, and wherein generating the respective combined score for each of the resources comprises:
            identifying a plurality of search results identifying the resource, wherein each search result identifying the resource is obtained from the search engine in response to a respective combined query, and wherein each search result identifying the resource is associated with a respective first score, and
            generating the combined score for the resource by combining the first scores associated with the search results identifying the resource; and
        ranking the obtained search results based on the combined scores for the respective resources identified by each search result.

2. The method of claim 1, wherein determining that the first search query includes a respective text reference to each of one or more predetermined attributes comprises:
    determining, only from text of the search query, that the first search query includes a respective text reference to each of one or more predetermined attributes.

3. The method of claim 1, further comprising:
    receiving the first search query from a user device; and
    providing the combined search results to the user device for presentation in a user interface.

4. The method of claim 3, wherein the combined search results are provided in place of search results obtained for the first search query.

5. The method of claim 1, wherein determining that the first search query includes a reference to one or more attributes associated with a first entity type comprises:
    determining that at least one term in the first search query appears in an attribute data store.

6. The method of claim 5, wherein the attribute data store contains terms from previously submitted queries determined to relate to entities of the first entity type by a query classifier.

7. The method of claim 1, further comprising:
    determining that, for a particular combined search result obtained in response to a particular combined query, a number of combined search results ranked higher than the particular combined search result in the ranking of the combined search results and obtained in response to the particular combined query exceeds a specified threshold number; and
    demoting the particular combined search result in the ranking of combined search results.

8. A non-transitory computer storage medium encoded with a computer program, the program comprising instructions that when executed by one or more computers cause the one or more computers to perform operations comprising:

determining that a first search query includes a respective text reference to each of one or more predetermined attributes, wherein each attribute is associated with a first entity type;

for each of a plurality of entities of the first entity type, generating a combined search query that includes the first search query and a name of the entity;

obtaining search results for each of the plurality of entities using the combined search query for each respective entity; and using the obtained search results to generate combined search results to include in a response to the first search query, wherein using the obtained search results to generate combined search results comprises:

generating a respective combined score for each of a plurality of resources identified by the obtained search results, wherein the respective combined score for each resource is a combination of scores associated with obtained search results identifying the resource, and wherein generating the respective combined score for each of the resources comprises:

identifying a plurality of search results identifying the resource, wherein each search result identifying the resource is obtained from the search engine in response to a respective combined query, and wherein each search result identifying the resource is associated with a respective first score, and generating the combined score for the resource by combining the first scores associated with the search results identifying the resource; and ranking the obtained search results based on the combined scores for the respective resources identified by each search result.

9. The non-transitory computer storage medium of claim 8, wherein determining that the first search query includes a respective text reference to each of one or more predetermined attributes comprises:

determining, only from text of the search query, that the first search query includes a respective text reference to each of one or more predetermined attributes.

10. The non-transitory computer storage medium of claim 8, the operations further comprising:

receiving the first search query from a user device; and providing the combined search results to the user device for presentation in a user interface.

11. The non-transitory computer storage medium of claim 10, wherein the combined search results are provided in place of search results obtained for the first search query.

12. The non-transitory computer storage medium of claim 8, wherein determining that the first search query includes a reference to one or more attributes associated with a first entity type comprises:

determining that at least one term in the first search query appears in an attribute data store.

13. The non-transitory computer storage medium of claim 12, wherein the attribute data store contains terms from previously submitted queries determined to relate to entities of the first entity type by a query classifier.

14. The non-transitory computer storage medium of claim 8, the operations further comprising:

determining that, for a particular combined search result obtained in response to a particular combined query, a number of combined search results ranked higher than the particular combined search result in the ranking of the combined search results and obtained in response to the particular combined query exceeds a specified threshold number; and demoting the particular combined search result in the ranking of combined search results.

15. A system comprising one or more computers and one or more storage devices storing instructions that when executed by the one or more computers cause the one or more computers to perform operations comprising:

determining that a first search query includes a respective text reference to each of one or more predetermined attributes, wherein each attribute is associated with a first entity type;

for each of a plurality of entities of the first entity type, generating a combined search query that includes the first search query and a name of the entity;

obtaining search results for each of the plurality of entities using the combined search query for each respective entity; and using the obtained search results to generate combined search results to include in a response to the first search query, wherein using the obtained search results to generate combined search results comprises:

generating a respective combined score for each of a plurality of resources identified by the obtained search results, wherein the respective combined score for each resource is a combination of scores associated with obtained search results identifying the resource, and wherein generating the respective combined score for each of the resources comprises:

identifying a plurality of search results identifying the resource, wherein each search result identifying the resource is obtained from the search engine in response to a respective combined query, and wherein each search result identifying the resource is associated with a respective first score, and generating the combined score for the resource by combining the first scores associated with the search results is the resource; and ranking the obtained search results based on the combined scores for the respective resources identified by each search result.

16. The system of claim 15, wherein determining that the first search query includes a respective text reference to each of one or more predetermined attributes comprises:

determining, only from text of the search query, that the first search query includes a respective text reference to each of one or more predetermined attributes.

17. The system of claim 15, the operations further comprising:

receiving the first search query from a user device; and providing the combined search results to the user device for presentation in a user interface.

18. The system of claim 17, wherein the combined search results are provided in place of search results obtained for the first search query.

19. The system of claim 15, wherein determining that the first search query includes a reference to one or more attributes associated with a first entity type comprises:

determining that at least one term in the first search query appears in an attribute data store.

20. The system of claim 19, wherein the attribute data store contains terms from previously submitted queries determined to relate to entities of the first entity type by a query classifier.

21. The system of claim 15, the operations further comprising:

determining that, for a particular combined search result obtained in response to a particular combined query, a number of combined search results ranked higher than the particular combined search result in the ranking of the combined search results and obtained in response to the particular combined query exceeds a specified threshold number; and demoting the particular combined search result in the ranking of combined search results.

* * * * *